Figure 1:
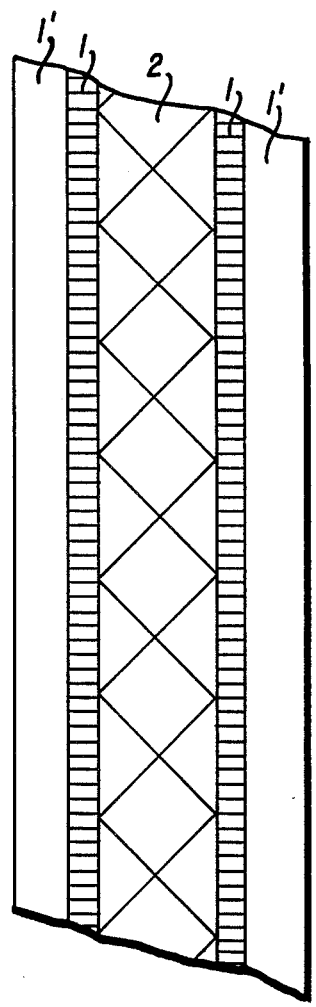

United States Patent [19]
Capizzi et al.

[11] Patent Number: 4,879,837
[45] Date of Patent: Nov. 14, 1989

[54] DEVICE DEVELOPING AN ATTRACTIVE AND TOXIC ACTION FOR FIGHTING INSECTS

[75] Inventors: Amedeo Capizzi; Emilio Arsura; Pia Spinelli, all of Milan, Italy

[73] Assignee: Istituto Guido Donegani S.p.A., Novara, Italy

[21] Appl. No.: 142,245

[22] Filed: Jan. 5, 1988

Related U.S. Application Data

[63] Continuation of Ser. No. 843,723, Mar. 25, 1986, abandoned.

[30] Foreign Application Priority Data

Mar. 25, 1985 [IT] Italy ............................ 20054 A/85

[51] Int. Cl.$^4$ .............................................. A01M 1/20
[52] U.S. Cl. ..................................................... 43/124
[58] Field of Search .................... 43/132.1, 124, 131; 424/16

[56] References Cited

U.S. PATENT DOCUMENTS

| | | | |
|---|---|---|---|
| 3,826,036 | 7/1974 | Neugebauer | 43/132.1 |
| 3,972,993 | 8/1976 | Kobayashi | 43/131 |
| 4,227,333 | 10/1980 | Levinson | 43/132.1 |

FOREIGN PATENT DOCUMENTS

| | | | |
|---|---|---|---|
| 2503537 | 10/1982 | France | 43/132.1 |
| 142531 | 12/1978 | Japan | 43/132.1 |
| 142533 | 12/1978 | Japan | 43/132.1 |
| 142202 | 11/1981 | Japan | 43/132.1 |

Primary Examiner—Gene P. Crosby
Attorney, Agent, or Firm—Stevens, Davis, Miller & Mosher

[57] ABSTRACT

There is described a device which develops an attractive and toxic action for combatting insects, consisting of a substrate of fibers and/or fibrils containing, either in an adsorbed or dispersed form, a pheromone, and which is partially coated with a layer impermeable to the phermone, the layer carrying, adhering to its external surface, an insecticide or a substrate impregnated with an insecticide.

3 Claims, 1 Drawing Sheet

DEVICE DEVELOPING AN ATTRACTIVE AND TOXIC ACTION FOR FIGHTING INSECTS

This application is a continuation of application Ser. No. 843,723, filed Mar. 25, 1986, now abandoned.

BACKGROUND OF THE INVENTION

The present invention relates to a device having an attractive and poisonous action for combatting insects, and more particularly concerns a device which both releases pheromones and develops an insecticide action, and by the use of which device it is possible to attract and eliminate adult insects.

For the past ten years pheromones have gained great importance in the field of research for new methods for controlling species of insects noxious to agricultural cultivations; when compared to conventional products, said substances have the advantage of offering a considerable selectivity towards one specific or a limited number of kindred species of insects, without thereby involving the harmless or even useful fauna.

It is thus possible to fight a certain parasite with the help of pheromones without thereby disturbing the surrounding ecological equilibrium.

The pheromones are secreted towards the outside of the body of the insects by special glands and, according to the type of reaction they induce, they may be subdivided into: aggregating, tracing, alarming or warning, sexually attracting, etc., hormones. The most diffused and most interesting for the possibilities they offer for the control of the noxious species of insects are the sexual pheromones which are secreted by the female, but in a number of species also by the male insect, and which attract the individuals of the opposite sex for the mating. Small quantities of such attractive pheromones obtained by synthesis awake the same reactions that are induced in the insects by the natural hormone.

The synthetic sexual pheromones are used both for watching the growth of the parasite populations and for directly controlling the noxious species by hindering the matings.

The first type of application (monitoring) allows to follow, by means of periodical drawings or samplings of the captured insects by special traps, the fluctuations of the parasite populations by watching their biological cycle and by forecasting the possible attainment of the "threshold of noxiousness".

On the basis of these data it is then possible to decide the opportunity and the moment for intervening with pesticides.

In the second type of application, the sexual pheromones may partially substitute or totally replace the insecticides and directly control the noxious species by interfering with their reproductive activity.

The techniques used for this purpose are two: the massive capture and the disorienting. The first consists in attracting and thus in capturing the greatest possible number of adult insects by means of special traps baited with the pheromone.

The second technique is realized by diffusing the attracting agent through the air in such a way as to hinder the insects in localizing the individuals of the opposite sex, thus hindering the matings.

The diffusion of the pheromone may be obtained by placing the product in various distinct and suitably distanced points of the cultivation to be protected, or by distributing the product uniformly over the whole area of interest. In the first case, there are used dispensers in which the active principle is incorporated in substrates of a different nature which control the releasing speed and the persistence. In the second case, there are used special formulations with a regulated releasing rate, which are applied from the ground or from the air.

Conceptually, the two systems of pheromone diffusion differ from one another inasmuch as, in the case of the localized dispensers, these simulate the recalling insect, thereby creating numerous false traces, while the uniformly diffused pheromone covers up the natural recalls of the insects thereby hindering their perception on the part of the individuals.

The first system is realized, for instance, with capillaries with an open end through which the active principle volatilizes (U.S. Pat. No. 4,017,030) while the second system is realized by microcapsules with polyamide walls (U.S. Pat. No. 3,577,515) or by a gel or jelly (U.S. Pat. No. 2,800,457 and U.S. Pat. No. 2,800,458) or again by special mixtures of absorbing and adsorbing powders (see U.S. Pat. No. 4,325,941).

These systems are used in the fight against parasites but allow to obtain satisfactory results only for a few species of insects and only in particular situations. In fact, if, for instance, the insects to be controlled are very mobile and their number is very high, there will be a considerably high probability of casual approaches between the individuals with a consequent loss of efficacy of the method.

Said risk may be reduced by increasing the number of the localized dispensers or the concentration of the uniformly distributed pheromone. Both solutions involve, however, an increased economical burden.

THE PRESENT INVENTION

An object of the present invention is to provide a device suited for releasing pheromones into the air in a way similar to that which occurs in nature, and which exerts a toxic action that will allow an effective control over the noxious species of insects both by means of an action of disorientation and by the attraction and elimination of the adult insects.

It has now been found that this object, among others, is achieved by a device or means consisting of a substrate of fibers and/or fibrils containing a pheromone in either an adsorbed or dispersed form, partially coated by a layer impermeable to the pheromone, said layer carrying adhered to its external surface, an insecticide or by impregnating said layer with an insecticide.

For the formation of both the pheromone containing substrate as well as of the substrate possibly containing the insecticide, any natural, artificial or synthetic fibers or fibrils may be used.

In practice, preference is given to fibers or fibrils that may be welded to the impermeable layer, such as polyethylene fibrils alone or in admixture with cellulose fibers.

The fibrous substrate may be in the form of paper, non-woven fabrics, felt, cloth, etc., and may be of any shape and size suitable for the purpose, i.e., in layers of square, rectangular or polygonal shape, or in the form of small cylinders, parallelepipedons or spheroids.

The impermeable coating layer may be a film of either aluminum, or nylon, polyester, polyvinylchloride, or of a polyolefin such as polypropylene, polyethylene, ethylene propylene copolymers, etc., either alone or coupled to each other or combined with other films in order to impart to said layer the desired properties.

The coating of the substrate, in order to allow the release of the pheromone, may be realized in various ways, for instance, provided with apertures of various shapes such as through-holes, notches ending in through-holes or, in case the coupling substrate/impermeable film is in stratified form, it may be formed by the free lateral surfaces of said coupling.

The device of the present invention may be prepared by sticking the fibrous substrate to the impermeable layer and by successively impregnating the so obtained stratified substrate with a pheromone solution, or by dispersing the pheromone in the fibrous substrate and by then adhering the impermeable layer to it, by successively applying to the impermeable surface of the thus prepared support an insecticide or by applying to it a substrate impregnated with an insecticide and finally by possibly making a number of apertures in it.

The adhesion of the first substrate and of the possible second insecticide-impregnated substrate to the impermeable layer may be obtained, for example, by glueing, thermo-sticking or by clinching.

In the case of thermo-sticking or welding, the temperature and pressure used for the purpose must be chosen in such a way as to avoid melting of the fibrous material and to preserve the desired porosity thereof.

The insecticides may be used either as such or formulated in powders, oils, microcapsules and the like.

The insecticide may be of any type but with the preference for those developing a fast contacticide action, such as, for instance: pyrethum, synthetic pyrethroids, carbamates, phospho-organic substances.

By the use of the device or means according to the present invention it is possible to realize an effective and selective method for fighting noxious adult insects by exploiting the disorienting and attracting action of pheromones released in a slow and controlled way, in combination with the toxic action of an insecticide on the attracted insect.

The accompanying drawing represents a preferred embodiment of the device according to this invention. In the drawing:

2 is a substrate of fibrils of polyethylene in admixture with cellulose fibers impregnated with pheromone;

1 is a layer impermeable to the pheromone carrying adhering to the external surface an insecticide or a substrate impregnated with insecticide (1'); and 1' is an insecticide or a substrate impregnated with an insecticide.

The following examples are given to further illustrate the present invention without limiting the spirit and scope thereof.

EXAMPLE 1

A sheet of paper 1.10 mm thick, containing 80% of polyethylene fibrils (FERLOSA—registered trademark of MONTEDISON) and 20% of cellulose with a specific weight of 380 g/m$^2$, was coated on both faces by pressing it in a die or mold 0.75 mm thick, at 115° C., together with a three-layered polyester-aluminum-polyethylene film, the three layers having, respectively, a thickness of 15 micron, 8 micron and 90 micron, laid out in such a way that the polyethylene layer was turned towards the paper.

Squares with 20 mm sides were cut from the stratified structure and were then impregnated by dipping into a 10% solution of cis-, trans- 9,12-tetradecadienyl acetate in dichloromethane, of sexual pheromones of different kindred species of Ficitide Leptidoptera of foodstuffs, of 2-hydroxy-4'-octyloxy-benzophenone (UV-stabilizer) and of 2,6-di-terbutylphenol propionate of pentaeritrile (an anti-oxidant).

After complete evaporation of the solvent, each square sample proved to contain about 2 mg of cis-, trans-9,12-tetradecadienyl acetate and 1 mg, respectively, of the stabilizer and the antioxidant.

To these squares were then coupled by glueing a square of the same size and prepared as follows.

A paper of the type described above, but with a thickness of 0.46 mm (220 g/m$^2$) was cut up into squares and impregnated with a dichloromethane solution containing 5% of technical cypermethrine (synthetic pyrethroid) and 10% of vaseline oil. Once evaporation of the solvent had been completed, each square proved to contain about 5 mg of cypermetrine and about 10 mg of vaseline oil.

The pheromone dispensers coupled to the insecticide-impregnated supports or carriers were applied by means of a biadhesive tape, in suitable spots (walls, ceilings, windows, pipes and braces, etc.), in the rooms of a mill located in Borghetto Lodigiano (Mi) which grinds soft wheat to flour for bread-making and which is infested all the year round by meal moth of Ephestia kuehniella. The couplings were distributed in a proportion of one about every 5 m$^2$ of walls and ceiling in 3 rooms of about 500 m$^3$ and located on different floors.

The experiment was conducted for the months of June and July. During that period no insecticide treatments were carried out in the mill. The efficacy of the method was assessed by appreciating at the start and successively evaluating every 15 days the number of Ephestia adults present on the walls and ceiling of the middle room (room of the refiner or cleanser). The data so obtained were compared with the data of similar control counts carried out on the walls of another room of similar dimensions (room of the sievers) placed above the other two rooms and not communicating with the same, and in which third room no dispensers had been distributed.

The data obtained from the periodical observations carried out for the 60 days of the test are recorded on the following Table I.

TABLE I

| Days lapsed since the start of the test | Mean number of adults per sq. mt. | |
|---|---|---|
| | Treated | Witness |
| 0 | 2.64 | 1.5' |
| 15 | 0.11 | 1.80 |
| 30 | 0.04 | 2.13 |
| 45 | 0.03 | 2.90 |
| 60 | 0.05 | 2.48 |

During the counts in the rooms in which dispensers had been distributed, there was noted the presence of numerous E. kuehniella that had dropped to the floor.

EXAMPLE 2

A Ferlosa paper 0.55 mm thick and containing 60% of polyethylene fibrils and 40% of cellulose (200 g/m$^2$), was coupled at 115° C., on both faces, with a film as used in Example 1. The resulting final coupling showed a thickness of 0.45 mm.

From said coupling there were drawn 24×24 mm square specimens which were dipped into a dichloromethane solution containing the pheromonic mixture of Cydia molesta (peach Cydia) in a concentration of 20% by weight and 1% of the stabilizer and anti-oxidizer cited in Example 1.

Each square, after complete evaporation of the solvent, proved to contain 1.86 mg of cis-8-dodecenyl acetate, 0.14 mg of trans-8-dodecenyl acetate, 0.02 mg of cis-8-dodecenol, 5 mg of dodecanol and 0.1 mg, respectively, of stabilizer and antioxidant.

There were then prepared squares of Ferlosa paper containing cyper metrine and vaseline oil according to the procedures described in Example 1.

By means of a clincher, the squares containing the pheromonic mixture and the squares with the insecticide were coupled together and contemporaneously applied to the branches of peach trees of a 2,500 m² plot (with 120 plants), located in Volpedo (AL), in a proportion of two squares per one tree.

In the center of the peach orchard there was placed a commercial trap "TRAPTEST" for the control of the C. molesta flights while a similar trap was placed in the center of a plot of similar size and located some 300 m away from the other trap.

The test, which was conducted from the beginning of May up to the end of August, was followed both by counting the captures in the pheromone traps as well as by evaluating the damages by samplings of the sprouts and fruits hit by the Cidia on the two lots.

During the 4 months test there were carried out two applications of the dispensers.

During said period, on the trap placed inside the area in which there had been distributed the pheromone dispensers coupled to the insecticide-carrying supports, there was noticed at the end of June the capture of only 3 males, which resulted in the decision to make a second application of dispensers, while in the trap placed in the witness peach orchard there was captured a total of 423 males.

The percentage of damaged sprouts at the end of June amounted to 1.46% in the zone or area in which the dispensers had been distributed, and to 9.24% in the witness lot that had not been submitted to any conventional treatment with insecticides.

At the picking time, the attack on the fruits amounted to 0.85% in the peach orchard protected with the dispensers and to 6.34% in the witness peach orchard.

EXAMPLE 3

A 1.10 mm thick paper containing 60% of polyethylene fibrils (Ferlosa) and 40% of cellulose (320 g/m²) was coupled at 105° C. on both faces to 0.08 mm thick film of low density polyethylene. The resulting coupling had a thickness of 0.75 mm and from this were drawn 10×10 mm squares that were dipped into a dichloromethane solution containing 15% cis-9-tricosene (Muscalure), an aggregation pheromone of Dipteros Musca domestica. After complete evaporation of the solvent, each square contained about 2 mg of cis-9-tricosene.

Successively, squares of yellow drawing paper 30×30 mm were impregnated, by dipping, with Baygon EC (20% of Propoxur, Bayer Italia S.p.A.).

In the center of each of these squares carrying the insecticide, there was glued on a small square impregnated with Muscalure.

The couplings were made to stick by means of a glue against the walls of a room (120 m³), empty and illuminated by natural light, in which the temperature varied from 20° C. during night hours and 25° C. during day hours. The relative humidity fluctuated around 60%. The dispensers were distributed in a proportion of one for every 10 m² of walls and ceiling. The test was started at 9 o'clock with the release into the above said room of 500 adult Muscaedomesticae 2-3 days old drawn at random out of a mixed population grown artifically.

The effectiveness of the method was assessed by 5 countings of the number of dead individuals, carried out at different times during the 48 hours succeeding the start of the test.

The results of the various countings carried out are recorded in the following Table II.

TABLE II

| Time lapsed from start of test | Number of dead adults |
|---|---|
| 3 hours | 127 |
| 10 hours | 316 |
| 24 hours | 352 |
| 32 hours | 438 |
| 48 hours | 473 |

After 48 hours from the start no live flies could be observed. The missing insects must be considered as having escaped during the test.

What we claim is:

1. A device for combating noxious insects, consisting of a substrate of fibrils in the form of a paper of polyethylene in admixture with cellulose fibers, containing in an either adsorbed or dispersed form a pheromone, said substrate being partially coated with a layer impermeable to the pheromone consisting of a film of a substance selected from the group consisting of polyolefin, aluminum, nylon, polyester, polyvinylchloride, either alone or in admixture each other, or with other films, said layer carrying adhering to its external surface an insecticide or a substrate impregnated with an insecticide.

2. A device for combating noxious insects, consisting of a substrate of fibers, fibrils, or a mixture of fibers and fibrils, containing in either an adsorbed or a dispersed form a pheromone, said substrate being partially coated with a layer impermeable to the pheromone, said impermeable layer being a film selected from the group consisting of polyolefins, aluminum, nylon, polyester, polyvinylchloride, either alone or in admixture with each other, or with other films, said layer carrying adhering to its external surface an insecticide or a substrate impregnated with an insecticide.

3. A device according to claim 2, characterized in that the substrate of fibers, fibrils, or mixtures of fibers and fibrils, is in the form of paper, a non-woven fabric, felt, or cloth, made of either natural, artificial or synthetic fibers or fibrils, or their mixtures.

* * * * *